United States Patent [19]

Devash

[11] Patent Number: 4,855,304

[45] Date of Patent: Aug. 8, 1989

[54] DINUCLEOSIDE PYROPHOSPHATES AND PYROPHOSPHATE HOMOLOGS AS PLANT ANTIVIRALS

[75] Inventor: Yair Devash, Winchester, Mass.

[73] Assignee: Repligen Corporation, Cambridge, Mass.

[21] Appl. No.: 786,260

[22] Filed: Oct. 10, 1985

Related U.S. Application Data

[63] Continuation-in-part of Ser. No. 690,929, Jan. 10, 1985, abandoned.

[51] Int. Cl.$^4$ .................. A61K 31/70; A61K 31/665
[52] U.S. Cl. .......................................... 514/47; 514/48; 514/51; 536/27; 536/28; 536/29; 47/58
[58] Field of Search ............... 536/27, 28, 29; 514/44, 514/42, 48, 51

[56] References Cited

U.S. PATENT DOCUMENTS 3,321,463  5/1967  Moffatt .................................. 536/27

OTHER PUBLICATIONS

England et al., Proc. Nat. Acad. Sci., USA, 74(11), 4839-4842, 1977.
Bartkiewicz et al., Chem. Abstr., 102, 185421d, 1984.
Stone, Chem. Abstr., 100, 34777g, 1984.
Ohtsuka et al., J. Chem. Soc., Perkin Trans I, 1985, 997-1000.
Bartkiewicz et al., Chem. Abstr., 102: 2366x, 1985.
Stone, Chem. Abstr., 98: 154915n, 1983.
Ohtsuka et al, Nucleic Acids Research, vol. 8, pp. 601-610, 1980.
Devash, Y., Hauschner, A., Sela, I. and Chakraburtty, K. (1981), "The Antiviral Factor (AVF) from Virus-Infected Plants Induces Discharge of Histidinyl-TMV-RNA Virology", 111: 103-112.
Devash, Y., Biggs, S. and Sela, I. (1982), "Multiplication of Tobacco Mosaic Virus in Tobacco Leaf Disks is Inhibited by (2'-5') Oligoadenylate", Science, 216: 1415-1416.
Devash, Y. et al. (1984), "5'-Dephosphorylated 2',5'-Adenylate Trimer and Its Analogs", Journ. Biol. Chem. 259: 3482-3486.
Lee, C., and R. J. Suhadolnik (1985), "2',5'-Oligoadenylates Chiral at Phosphorus: Enzymatic Synthesis, Properties, and Biological Activities of 2',5'-Phosphorothioate Trimer and Tetramer Analogs Synthesized from (Sp)-ATP$\alpha$S", Biochem. 24:3: 551-555.
Eckstein, F., P. H. Romaniuk, and B. A. Connolly (1982), "Stereochemistry of Enzymatic Phosphoryl and Nucleotidyl Transfer", Methods of Enzymology, 87: 197-212.
Knowles, J. R. (1980), "Enzyme Catalyzed Phosphoryl Transfer Reactions", Ann. Rev. Biochem., 1980, 49: 877-919.
Frey, P. A., J. P. Richard, H.-T. Ho, R. S. Brody, R. D. Sammons, and K.-F. Sheu (1982), "Stereochemistry of Selected Phosphotransferases and Nucleotidyltransferases", Methods in Enzymology, 87: 213-235.
Wood, R. K. S. (ed.), Active Defense Mechanisms in Plants, Plenum Press, New York and London.
Dawson, W. O. (1984), "Effects of Animal Antiviral Chemicals on Plant Viruses", Phytopathology, 74: 2: 211-213.
Kluge, S., and C. Oertel (1976), "Prufung von Virazol auf die Vermehrung des Gurkenmosaik-Virus (cucumber mosaic virus) und des Nelkenscheckungs-Virus (carnation mottle virus)", Arch. Phytopathol. u. Pflanzenschutz, 4: 219-225.
Mitteilung, J. (1979), "Dioxohexahydrotriazin, Eine Neue Vollsynthetische Antiphytovirale Verbindung", Zbl. Bakt. II. Abt. 134: 64-69.
Kassanis, B., and R. F. White (1975), "Polyacrylic Acid-Induced Resistance to Tobacco Mosaic Virus in Tobacco cv. Xanthi", Ann. Appl. Biol., 79: 215-220.
Stein, A., and G. Loebenstein (1972), "Induced Interference by Synthetic Polanions with the Infection of Tobacco Mosaic Virus", Phytopathology 62: 1461-1466.
Stein, A., G. Loebenstein and S. Spiegel (1979), "Further Studies of Induced Interference by a Synthetic Polyanion of Infection by Tobacco Mosaic Virus", Physiological Plant Pathology, 15: 241-255.
Smookler, M. M. (1971), "Properties of Inhibitors of Plant Virus Infection Occurring in the Leaces of Species in the Chenopodiales", Ann. Appl. Biol., 69: 157-168.
Tomlinson, J. A., V. M. Walker, T. H. Flewett and G. R. Barclay (1974), "The Inhibition of Infection by Cucumber Mosiac Virus and Influenza Virus by Extracts from *Phytolacca americana*", J. Gen. Virol., 22: 225-232.
Bartkiewicz, M., H. Sierakowska, and D. Shugar (1984), "Nucleotide Pyrophosphatase from Potato Tubers", Eur. J. Biochem., 143: 419-426.

*Primary Examiner*—Ronald W. Griffin
*Assistant Examiner*—L. Eric Crane
*Attorney, Agent, or Firm*—Roman Saliwanchik; David R. Saliwanchik

[57] ABSTRACT

Potent plant antivirals are disclosed along with their method of use. These antivirals, 5',5'- or 2',5'- or 3',5'-pyrophosphorylated-dinucleotides, are specifically shown to inhibit tobacco mosaic virus (TMV) replication in tobacco plants when applied to the leaves or through the roots of these plants. These antiviral compounds can also be used to treat a variety of other plants, as disclosed herein, which are susceptible to a broad range of viruses.

4 Claims, No Drawings

DINUCLEOSIDE PYROPHOSPHATES AND PYROPHOSPHATE HOMOLOGS AS PLANT ANTIVIRALS

CROSS REFERENCE TO A RELATED APPLICATION

This is a continuation-in-part of my copending application Ser. No. 690,929, filed on Jan. 10, 1985, now abandoned.

BACKGROUND OF THE INVENTION

Plant viral diseases are numerous, and many of them are of the most virulent type. These diseases take a toll measured in the billions of dollars each year. Such viral diseases are particularly hard to control and virtually impossible to cure. One plant virus can attack many different species of plants and be carried by a large number of different vectors (insects, nematodes, fungi, parasitic vascular plants and agricultural tools). Viruses can also be transmitted from one generation to another through the seed, and some viruses are soil borne.

In mammals, interferon is the most rapidly produced defense mechanism against viral infection. One of the activities induced by interferon in mammalian cells is the conversion of ATP to a series of unique 2′,5′-oligoadenylates (Pestka, S. [ed] [1981] Methods in Enzymology, Vols. 78 and 79, Academic Press, New York). Similar, but not identical, plant oligonucleotides are induced by AVF (antiviral factor, or plant interferon) in tobacco plants following tobacco mosaic virus (TMV) infection (Devash, Y. et al. [1981] Virology 111: 103-112).

Recently it was reported that the naturally occurring 2′,5′-oligoadenylates, as well as the chemically synthesized 2′,5′-oligonucleotide analogs, are potent inhibitors of TMV replication at the nanomolar ($10^{-9}$M) level (Devash, Y., Biggs, S., and Sela, I. [1982] Science 216: 1415-1416; Devash, Y. et al. [1984] Jour. Biol. Chem. 259: 3482-3486).

BRIEF SUMMARY OF THE INVENTION

The subject invention concerns the use of nucleotides conjugated by pyrophosphoryl linkages as plant antivirals. Specifically exemplified is the use of dinucleotide 5′,5′-$p^1$,$p^2$-diphosphate, diadenosine 2′,5′-$p^1$,$p^2$-diphosphate and diadenosine 3′,5′-$p^1$,$p^2$-diphosphate to inhibit TMV replication in tobacco plants when applied to the leaves or through the roots of said plants. Application of these antiviral compounds through the roots of a tobacco plant or onto the plant leave results in the inhibition of TMV replication.

DETAILED DISCLOSURE OF THE INVENTION

The conjugated nucleotides of the subject invention, which can be used to inhibit plant virus replication, are known and available compounds, or compounds which can be readily prepared by procedures well known in the art. These conjugated dinucleotides can be shown by general formulae I-III of Chart A, where $X_1$ is A or C or D or E, and $X_2$, $X_3$ are B or C or D or E; $R_1$ and $R_2$ are purines or pyrimidines, or their analogs; $R_3$, $R_4$, $R_5$, $R_6$, $R_7$, $R_8$, $R_9$ and $R_{10}$ are H, OR′, NR′R″, (wherein R′ and R″ can be the same or different and are H or alkyl of 1 to 4 carbon atoms), an amino acid,

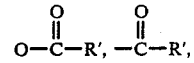

halogen, COOR″, —SO4, or —PO4; $R_{11}$ is P or P—O$^{(-)}$ or S=O or S; $R_{12}$ is O or S; $R_{13}$ and $R_{16}$ are O, S, CH2, or Se; $R_{14}$ and $R_{15}$ are O, CH2; $R_{17}$, $R_{18}$, $R_{19}$ and $R_{20}$ are H, OH, NH2CH3; $R_{21}$, $R_{22}$ are H, OH,

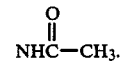

n in I, II, or III is an integer from 2 to 3 and n′ is an integer from 4 to 16.

Examples of purines and pyrimidines are adenine, guanine, cytosine, uracil, thymine, and the like.

Examples of purine and pyrimidine analogs are 6-dimethylaminopurine, 6-methoxypurine, 8-azaadenine, 2-chloropurine, 5-azacytosine, the aglycons of sangivamycin, toyocamycin, formycin, and tubercidin, 8-bromopurine, and 1, $N^6$-ethenoadenine. These purine and pyrimidine nucleotides are commercially available (Sigma Chemical Co., St. Louis, MO) and can be condensed into pyrophosphorylated plant antiviral dinucleotides chemically, using the methodology disclosed herein.

Halogens can be chlorine, bromine, iodine, and fluorine.

Amino acid can be any one of the twenty D- or L-common amino acids, i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The mono- , di- or triphosphates of the following nucleosides are suitable precursors for the synthesis of pyrophosphorylated plant antiviral nucleotides within the scope of formula I, such as: adenosine, 2′- or 3′-deoxyadenosine, 2′- or 3′-acetamido-β-D-ribofuranosyladenine, 2′- or 3′-amino-3′-deoxy-β-D-ribofuranosylcytosine, 1-β-D-xylofuranosylguanine, and 1-β-D-arabinofuranosyluridine. These nucleotides are commercially available (Sigma) and can be condensed into dinucleotide m,5′-$p^1$, $p^n$ (m=2′ or 3′; n=2—3) n-phosphates chemically, using the procedures disclosed herein, or other well-known procedures.

The precursors for the organic synthesis of the antiviral compounds, i.e., nucleotide-2′ or -3′ or -5′ monophosphates, are commercially available (Sigma).

The integer n denotes the repeating internal 2′,5′-, or 3′,5′- or 5′,5′-diester linkage of the dinucleotide.

The pyrophosphorylated plant antiviral dinucleotides can be prepared chemically essentially as described in Reiss, J. R. and Moffatt, I. G. (1965) J. Org. Chem 30: 3381-3387; Grummt, F. (1978) Proc. Natl. Acad. Sci. USA 76: 6081-6085; Kozarich, J. W. et al. (1973) Biochemistry 12: 4458-4463; Hoaro, D. E. and Ott, D. G. (1965) J. Amer. Chem. Soc. 87: 1785-1788; Hong et al. (1985) J. Med. Chem. 28: 171-177; DeHeras et al. (1985) J. Med. Chem. 28: 40-46; Black et al. (1985) Nucleoside and Nucleotide 4: 165-167. Using the chemical synthesis mentioned above a broad range of phosphorylated dinucleotide $p^1$, $p^n$ (n=2—3) n-phosphates can be prepared varying the nucleotide and its mono-, di-, and tri-phosphate moieties. Examples of such compounds are as follows: diadenosine 5',5'''-p$^1$,p$^2$-diphosphate (Ap$_2$A), diadenosine 5',5'''-p$^1$,p$_3$-triphosphate (Ap$_3$A), diadenosine 5',5'''-p$^1$,p$^4$-tetraphosphate (Ap$_4$A), diadenosine 5',5'''-p$^1$,p$^5$-pentaphosphate (Ap$_5$A), and diadenosine 5',5'''-p$^1$,p$^6$-hexaphosphate (Ap$_6$A) (all available from Sigma); and adenosine 5',5'''-p$^1$,p$^2$-diphospho-guanosine (Ap$_2$G), adenosine 5',5'''-p$^1$,p$^2$-diphospho-uridine (Ap$_2$U), adenosine 5',5'''-p$^1$,p$^2$-diphospho-cytidine (Ap$_2$C), 2',3'-cyclic phospho-diadenosine 5',5'''-p$^1$,p$^2$-diphosphate (p<Ap$_2$A>p), guanosine [5'] triphosphate adenosine (Gp$_3$A), thymidine [5'] diphosphate adenosine (TpA), cytosine [5'] tetraphosphate cytosine (Cp$_4$C), adenosine 3',5'-diphospho-adenosine (A3'pp5'A), adenosine 3',5'-diphospho-cytidine (A3'pp5'C), adenosine 3',5',diphospho-guanosine (A3'pp5'G), adenosine 2',5'-diphospho-adenosine (A2'pp5'A), adenosine 2',5'-diphospho-cytidine (A2'pp5'C) adenosine 2',5'-diphospho-guanosine (A2'pp5'G), and the like.

The most preferred compounds are: diadenosine 5',5'''-p$^1$,p$^2$-diphosphate (Ap$_2$A), adenosine 5',5'''-p$^1$,p$^2$-diphospho-guanosine (Ap$_2$G), adenosine 5',5'''-p$^1$,p$^2$-diphospho-uridine (Ap$_2$U), adenosine 5',5'''-p$^1$,p$^2$-diphospho-cytidine (Ap$_2$C), 2',3'-cyclic phospho-diadenosine 5',5'''-p$^1$,p$^2$-diphosphate (p<Ap$_2$A>p) and adenosine 5',5'-diphospho-thymidine.

The second most preferred compounds are: adenosine 2',5'-diphospho-adenosine (A2'pp5'A), adenosine 2',5'-diphospho-guanosin (A2'pp5'G), adenosine 2',5'-diphospho-uridine (A2'pp5'U), adenosine 2',5'-diphospho-cytidine (A2'pp5'C) and adenosine 2',5'-diphospho-thymidine (A2'pp5'T).

The third most preferred compounds are: adenosine 3',5'-diphospho-adenosine (A3'pp5'A), adenosine 3',5'-diphospho-guanine (A3'pp5'G), adenosine 3',5'-diphospho-uridine (A3'pp5'U), adenosine 3',5'-diphospho-cytidine (A3'pp5'C), and adenosine 3',5'-diphospho-thymidine (A3'pp5'T).

All the above compounds are available from P-L Biochemicals, Milwaukee, WI.

Upon applying an effective plant antivirus replication amount of a phosphorylated-dinucleotide to a plant susceptible to plant virus infection, the treated plant is able to withstand viral attack. Though the invention process is exemplified herein by use of the tobacco plant and TMV, it should be understood that the subject invention process can also be used to treat a variety of plants, for example, tobacco, barley, beans, oats, peas, soybeans, sugarbeets, sugarcane, wheat, alfalfa, cherries, citrus, grapes, melons, cucumbers, lettuce, peppers, potatoes, cocoa, coconut, and the like, susceptible to a broad range of viruses, for example, tobacco mosaic, vein banding, stripe mosaic, yellow dwarf, yellow mosaic, common mosaic, curly top, soil-borne mosaic, bud blight, streak mosaic, leaf roll, bean pod mottle virus, tobacco ringspot virus, peanut stunt virus, peanut mottle virus, maize dwarf mosaic disease complex, soybean mosaic virus, alfalfa mosaic virus, cucumber mosaic virus, tomato ringspot virus, and the like.

An "effective plant antivirus replication amount of a phosphorylated-dinucleotide" is readily ascertained for different plants, and viruses, by use of procedures disclosed herein, or by procedures known in the art. This determination can be readily done without undue experimentation. Following is a disclosure of materials and methods used in the invention.

1. Plants

*Nicotiana glutinosa* and *N. tabacum* var. samsum plants were grown in potting medium in greenhouse conditions (25±3° C., and constant illumination). The plants were fertilized with a commercial fertilizer every two weeks. Plants were used at 5–8 leaf stage (Devash, Y., Biggs, S. and Sela, I. [1982] Science 216: 1415–1416; Devash, Y. et al. [1984] Jour. Biol. Chem. 259: 3482–3486).

2. Antiviral Activity in TMV-Infected Leaf Discs

Assays for antiviral activity in TMV-infected leaf discs were done using leaves of *N. tabacum* var. samsun in which TMV is systemically spread. Leaves were mechanically inoculated with purified TMV (5 μg/ml in 0.01M sodium phosphate buffer, pH 7.6, containing 0.1 g/ml of carborundum as an abrasive). Immediately after infection, leaf discs (6.5 mm diameter) were punched out of the inoculated leaves and placed in a beaker containing 0.01M sodium phosphate, pH 7.6.

Calcium coprecipitation technique—Groups of 20 discs were selected at random from this common pool and placed onto separate petri dishes, each containing 18 ml of 10 mM 4-(2-hydroxyethyl)-1-piperazine ethanesulfonic acid (HEPES)-KOH, pH 7.05, 188 mg/L Na$_2$HPO$_4$—7H$_2$O. Discs were treated with the antiviral dinucleotides for 1 hr by adding the compounds together with 2 ml of 600 mM CaCl$_2$. At the end of the 1 hr incubation, the buffer containing the antiviral dinucleotide was replaced by a buffer lacking the antiviral dinucleotide for another hr. The discs were then washed with 0.01M sodium phosphate, pH 7.6, and were allowed to incubate for an additional 72 hr in phosphate buffer (Devash, Y., Biggs, S. and Sela, I. [1982] Science 216: 1415–1416; Devash, Y. et al. [1984] J. Biol. Chem. 259: 3482–3486). The discs were homogenized in 0.01M sodiuM phosphate buffer, pH 7.6, and the TMV content was determined by enzyme-linked immunosorbent assay (ELISA) as described below.

3. Antiviral Activity Determination Using Infectivity Tests

The ability of the antiviral dinucleotides to inhibit TMV replication in intact *N. glutinosa* plants (containing N-gene for TMV localization) was determined by infectivity tests. Solutions containing 5 μg/ml TMV, 0.1 μg/ml carborundum, and antiviral dinucleotide were applied to 5 half-leaves of *N. glutinosa*. The opposite half-leaves served as controls and were inoculated with infecting solution containing TMV and carborundum but no dinucleotides. The infection was allowed to proceed 48 hr. Inhibition of TMV replication was calculated as the percent of local lesions produced in antiviral compound treated half-leaves, as compared to control half-leaves.

4. Antiviral Activity on *N. Tabacum* Intact Plants

*Nicotiana tabacum* plants were used as a source of plant tissue in which TMV is spread systemically. These plants do not contain the N-gene for TMV localization.

(a) Root application: *N. tabacum* plants were removed from their pots and transferred into 50 ml tubes containing 10 ml of 10 mM HEPES-KOH, pH 7.6, and the antiviral dinucleotides. Two hr later, plants were transferred into 50 ml tubes lacking the antiviral compound and were inoculated by TMV as described above. Twenty-four hr later leaves were homogenized in 0.01M sodium phosphate buffer, pH 7.6, (1 g leaves/3 ml buffer) and TMV content was determined by ELISA.

(b) Leaf application: Antiviral activity was determined as described above but the *N. tabacum* plant was used. Twenty-four hr later the half-leaves were removed, homogenized and TMV content was determined by ELISA.

5. Enzyme-Linked Immunosorbent Assay (ELISA)

The TMV content of the homogenates was determined by ELISA essentially by the method of Clark and Adams ([1977] J. Gen. Virol. 34: 475–483) but with the following order of layers on the microtiter plates.

(a) the γ-globulin fraction of a serum obtained from a chicken immunized against TMV was absorbed directly to the plate.

(b) The next layer was the tested sample (at various dilutions) or a series of purified TMV suspensions at known concentrations (calibration curve).

(c) The third layer was the γ-globulin from the serum of a TMV-immunized rabbit.

(d) The final layer was goat antibody to rabbit immunoglobulin G conjugated with alkaline phosphatase (Sigma). The release of phosphate from p-nitrophenyl phosphate due to the antibody-conjugated alkaline phosphatase was monitored spectrophotometrically with a Microplate reader (Dynatech Diagnostics, Inc. South Windham, ME) and was proportional to TMV concentration in a log linear manner for about two logs (<2 ng to >200 ng). (Devash, Y., Biggs, S. and Sela, I. [1982] Science 216: 1415–1416)

6. Antibodies Against TMV

The γ-globulin fraction of serum obtained from chickens and rabbits immunized against TMV were generous gifts from Professor Ilan Sela, The Hebrew University of Jerusalem, Agriculture Faculty, Rehobot, Israel.

Following are examples which illustrate procedures, including the best mode, for practicing the invention. These examples should not be construed as limiting.

EXAMPLE 1

$5',5'$-$p^1,p^n$ (n=2—3)-Dinucleotide Antiviral Activity in TMV-Infected Tobacco Leaf Discs The $5',5'$-$p^1,p^n$ (n=2—3)-dinucleotides are as effective as the $2',5'$-adenylate trimer core in inhibiting TMV replication in TMV-infected discs (Table 1). As demonstrated, the calcium phosphate coprecipitation technique is essential for potentiation of the dinucleotides in the TMV-infected disc assay. However, the calcium coprecipitation technique was needed only in the disc assay and not in the other inhibitory activity measurements disclosed above.

The results in Table 1 indicate that in the disc assay the calcium coprecipitation technique potentiates the antiviral compounds by increasing their uptake. Table 1 also demonstrates the importance of calcium coprecipitation in the potentiation of antiviral dinucleotide in the TMV-infected leaf discs assay. The results indicate that the coprecipitation technique increases the uptake of the antiviral dinucleotides.

The $5',5'$-$p^1,p^n$ (n=2—3)-dinucleotides containing n=4 or more internal phosphates were less antivirally active as compared to dinucleotides with 2 and 3 internal phosphates. However, a modification in the nucleotide moiety (i.e., a replacement of one of the adenosines with G,C,U; an addition of external phosphates; or an addition of external $2',3'$-cyclic phosphate such as P<A5'PP5'A>P) did not decrease their antiviral potency.

TABLE 1

Inhibition of TMV Replication in TMV-Infected Leaf Discs by $5',5'$-$p^1,p^n$ (n = 2-3)-Dinucleotides and $2',5'$-Oligoadenylate

| | Treatment with [Ca$^{+2}$] Coprecipitation | | Treatment without [Ca$^{+2}$] Coprecipitation | |
|---|---|---|---|---|
| | 100 nM | 200 nM | 100 nM | 200 nM |
| Control | 75$^a$;0$^b$ | 75;0 | 56;0 | 56;0 |
| 2',5'ApApA | 46;39 | 36;52 | 53;5 | 48;14 |
| A5'pp5'A | 48;36 | 44;41 | N.I.;0 | N.I.;0 |
| A5'ppp5'A | 65;13 | 38;50 | N.I.;0 | N.I.;0 |

$^a$ngTMV/ml
$^b$percent inhibition as related to control
N.I. = no inhibition

EXAMPLE 2

$5',5'$-$p^1,p^n$ (n=2—3)-Dinucleotide Antiviral Activity in *N. glutinosa* Intact Plants The ability of the $5',5'$-dinucleotides to inhibit TMV replication in intact plants was tested using *N. glutinosa* plants. The $5',5'$-dinucleotides inhibited the TMV replication as demonstrated by the inhibition of formation of local lesions following infection (Table 2).

Of utmost interest is the fact that an application of A5'ppA, A5'ppp5'A, A5'pp5'C, and A5'pp5'G at a concentration of 1 μM (10$^{-6}$M) resulted in an induced resistance to TMV infection even in the non-treated half-leaf (Table 2).

The number of local lesions of the non-treated half-leaves was decreased as compared to the controls. Therefore, the antiviral compounds induced an antiviral resistance in the plant tissue even without a direct application.

TABLE 2

$5',5'$-$p^1,p^n$ (n = 2-3)-Dinucleotide Antiviral Activity in *N. glutinosa* Intact Plants

| | 10 nM (10$^{-8}$ M) | | 100 nM (10$^{-7}$ M) | | 1000 nM (10$^{-6}$ M) | |
|---|---|---|---|---|---|---|
| Treatment | Treated | Non-Treated | Treated | Non-Treated | Treated | Non-Treated |
| 2',5'-ApApA | 88.8 | 48.6 | 89.4 | 9.8 | 100 | 100 |
| A5'pp5'A | 96.0 | 68.4 | 95.4 | 54.6 | 100 | 100 |
| A5'ppp5'A | 98.6 | 80.3 | 100 | 100 | 100 | 100 |
| A5'pp5'G | 84.8 | 59.8 | 89.5 | 44.7 | 100 | 100 |
| A5'pp5'C | 55.0 | 36.1 | 51.9 | 35.5 | 63.5 | 32.9 |
| A5'pp5'U | 38.1 | 5.2 | 0 | 0 | 80.2 | 21.0 |

Note:
The above results are percent protection as compared to control TMV-infected leaves.

EXAMPLE 3

Root Application of 5',5'-$p^1,p^n$ (n=2−3)-Dinucleotides

In order to establish the relationship of the induced resistance to the N-gene for viral localization and to the transmission ability of the compounds, a comparison between leaf application and root application of antiviral dinucleotides to *N. tabacum* plants was made. *N. tabacum* plants were removed into vials containing 10 ml of 10 mM HEPES-KOH, pH 7.6, and 1 μM of antiviral dinucleotide. The plant roots were allowed to remain in the solutions for 2 hr and then were transferred to vials containing the buffer without the antiviral compounds.

The plants then were infected with TMV as above. (See section 4. Antiviral activity on *N. tabacum* intact plants, paragraph [a].) Another group of *N. tabacum* plants was tested as described in the above-noted section, paragraph (b).

Exposure of plant roots to 1 μM ($10^{-6}$M) of 2',5'ApApA, A5'pp5'A, or A5'pp5'G resulted in total suppression (98–100% inhibition) of the virus (Table 3). The induced resistance in leaf areas which were not directly treated with the antiviral dinucleotide is not attributed to the N-gene because the resistance was observed also in *N. tabacum* plants.

TABLE 3

| Application of Antivirals Through Roots | | |
|---|---|---|
| Treatment (2 hr) | ng TMV/g of leaves | % Protection |
| Control | 200 | 0 |
| 1 μM 2',5'ApApA | 0 | 100 |
| 1 μM A5'pp5'A | 0 | 100 |
| 1 μM A5'ppp5'A | 98 | 51 |
| 1 μM A5'pp5'G | 4 | 98 |

EXAMPLE 4

3',5'-$p^1,p^2$-Dinucleotide Antiviral Activity in TMV-Infected Tobacco Leaf Discs The 3',5'-$p^1,p^2$-dinucleotides are as effective as the 2',5'-adenylate trimer core in inhibiting TMV replication in TMV-infected discs (Table 4).

TABLE 4

Inhibition of TMV Replication in TMV-Infected Leaf Discs by 3',5'-$p^1,p^2$-Diadenosine Pyrophosphate and by 2',5'-ApApA

| Treatment | ng TMV/ml | % Inhibition as Related to Control |
|---|---|---|
| Control | 550 | 0 |
| 2',5'ApApA | | |
| 2 × $10^{-9}$ M | 200 | 64 |
| 20 × $10^{-9}$ M | 180 | 67 |
| 200 × $10^{-9}$ M | 100 | 82 |
| A3'pp5'A | | |
| 2 × $10^{-9}$ M | 550 | 0 |
| 20 × $10^{-9}$ M | 200 | 64 |
| 200 × $10^{-9}$ M | 150 | 73 |

The results in Table 4 demonstrate that at equivalent concentrations the A3'pp5'A and the 2',5'ApApA confer similar antiviral state.

EXAMPLE 5

A3'pp5'A Antiviral Activity in *N. glutinosa* Intact Plants

The A3'pp5'A ability to inhibit TMV replication in intact plants was tested using *N. glutinosa* plants. The A3'pp5'A inhibited the TMV replication as demonstrated by the inhibition of the formation of local lesions following infection (Devash, Y. et al. [1984] J. Biol. Chem. 259: 3482–3486). An application of A3'pp5'A at concentrations of 1 μM in the infection solution resulted in an induced resistance to TMV infection even in the non-treated half-leaf (Table 5).

TABLE 5

| A3'pp5'A Antiviral Activity in *N. glutinosa* Intact Plants | | |
|---|---|---|
| Treatment | Non-Treated Half Leaf | Treated Half Leaf |
| Control | 0 | 0 |
| $10^{-6}$ M 2',5'-ApApA | 90 | 100 |
| $10^{-6}$ M A3'pp5'A | 93 | 100 |

Note:
The above results are percent protection as compared to control TMV-infected leaves.

EXAMPLE 6

2',5'-$p^1,p_2$-Diadenosine Antiviral Activity

The 2',5'-$p^1,p^n$-diadenosine is an effective inhibitor of TMV replication in TMV-infected discs (Table 6).

TABLE 6

| Inhibition of TMV Replication in TMV-Infected Leaf Discs by 2',5'-$p^1,p^2$-Diadenosine | |
|---|---|
| Treatment | % Inhibition |
| Control | 0[b] |
| Adenosine 2',5'-$p^1,p^2$-diadenosine: | |
| $10^{-10}$ M | 0 |
| $10^{-9}$ M | 21 |
| $10^{-8}$ M | 26.4 |
| $10^{-7}$ M | 37 |
| $10^{-6}$ M | 42 |

[b]percent inhibition as related to control

The above results demonstrate (1) the antiviral potency of m to 5'-$p^1,p^n$-(m=2',3',5'; n=2−3)-dinucleotides, (2) the advantage of root application (i.e., application via irrigation), which is probably attributable to an active transport of the phosphate-containing compounds, and (3) the property of the m to 5'-$p^1,p^n$-(m=2',3',5'; n=2−3) dinucleotides to induce resistance to viral infection even in plant areas which were not directly treated (due to active rapid transport or a triggered antiviral state).

It is important to note that the application of the antiviral compounds in the range of $10^{-9}$ to $10^{-6}$M resulted in a total inhibition of the virus without any apparent plant toxicity.

CHART A $R_1$, $R_5$, $R_7$, $R_3$, $R_9$, $R_{18}$, $R_{14}$, $R_{20}$, $CH_2-R_{16}-[R_{11}-R_{13}]_n -X_1$    $X_1$ = A, C, D, E    n = 2-3    I $\begin{bmatrix} R_{12} \\ \| \\ R_{11}-R_{13} \end{bmatrix}$ -continued
CHART A

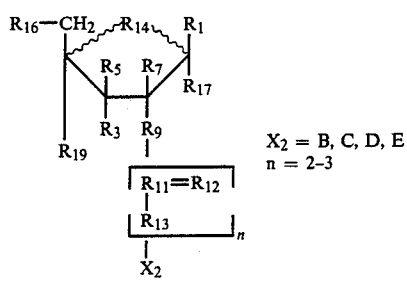

X₂ = B, C, D, E
n = 2-3

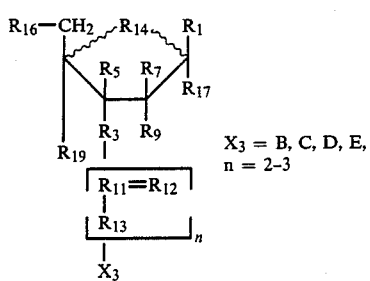

X₃ = B, C, D, E,
n = 2-3

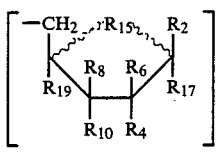    A

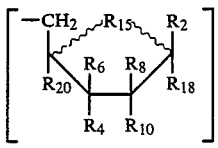    B

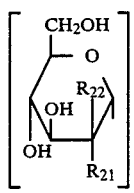    C

[CH₃(CH₂)$_{n'}$·CH₂—]   n' = 4-16    D

-continued
CHART A

    E

I claim:

1. A method, for inhibiting plant virus replication in a susceptible plant which comprises treating said plant with an effective plant antivirus replication amount of a 5',5'-dinucleotide of the formula

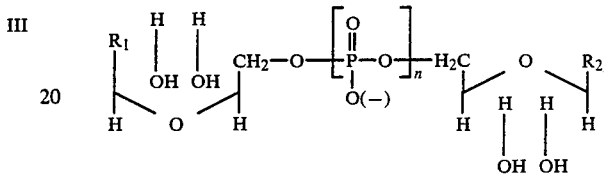    III wherein $R_1$ and $R_2$ are purines or pyrimidines, or their analogs, and n is an integer of 2 to 3.

2. A method, according to claim 1, wherein said 5',5'-dinucleotide is diadenosine 5',5'''-p¹,p²-diphosphate (Ap₂A), adenosine 5',5'''-p¹,p²-diphospho-guanosine (Ap₂G), adenosine 5',5'''-p¹,p²-diphospho-uridine (Ap₂U), adenosine 5',5'''-p¹,p²-diphospho-cytidine (Ap₂C), 2',3'-cyclic phospho-diadenosine 5',5'''-p¹,p²-diphosphate (p<Ap₂A>p) and adenosine 5',5'-diphospho-thymidine (Ap₂T).

3. A method for inhibiting plant virus replication in a susceptible plant which comprises treating said plant with an effective plant anti-virus replication amount of a 2',5'-dinucleotide selected from the group consisting of adenosine 2',5'-diphospho-adenosine (A2'pp5'A), adenosine 2',5'-diphospho-guanosine (A2'pp5'G), adenosine 2',5'-diphospho-uridine (A2'pp5'U), adenosine 2',5'-diphospho-cytidine (A2'pp5'C) and adenosine 2',5'-diphospho-thymidine (A2'pp5'T).

4. A method for inhibiting plant virus replication in a susceptible plant which comprises treating said plant with an effective plant anti-virus replication amount of a 3',5'-dinucleotide selected from the group consisting of adenosine 3',5'-diphospho-adenosine (A3'pp5'A), adenosine 3',5'-diphospho-guanine (A3'pp5'G), adenosine 3',5'-diphospho-uridine (A3'pp5'U), adenosine 3',5'-diphospho-cytidine (A3'pp5'C) and adenosine 3',5'-diphospho-thymidine (A3'pp5'T).

* * * * *

UNITED STATES PATENT AND TRADEMARK OFFICE
CERTIFICATE OF CORRECTION

PATENT NO. : 4,855,304

DATED : August 8, 1989

INVENTOR(S) : Yair Devash

It is certified that error appears in the above-identified patent and that said Letters Patent is hereby corrected as shown below:

Column 3: line 2: "-$p^1$, p3 -triphosphate" should read --$p^1,p^3$-triphosphate--

Signed and Sealed this

Eighteenth Day of December, 1990

Attest:

HARRY F. MANBECK, JR.

Attesting Officer

Commissioner of Patents and Trademarks